United States Patent [19]

Nakagawa et al.

[11] Patent Number: 5,731,431
[45] Date of Patent: Mar. 24, 1998

[54] PROCESS FOR PREPARING 4-SUBSTITUTED AZETIDINONE DERIVATIVES

[75] Inventors: Yuuki Nakagawa, Toyama; Kiyohito Imai, Niigata; Tamio Hara, Toyama, all of Japan

[73] Assignee: Nippon Soda Co., Ltd., Tokyo, Japan

[21] Appl. No.: 664,969

[22] Filed: Jun. 10, 1996

Related U.S. Application Data

[63] Continuation of Ser. No. 436,639, May 8, 1995, abandoned, which is a continuation of Ser. No. 108,641, filed as PCT/JP92/01698 filed on Dec. 25, 1992, abandoned.

[30] Foreign Application Priority Data

Dec. 26, 1991 [JP] Japan ..................... 3-356830
May 28, 1992 [JP] Japan ..................... 4-160080
Jul. 23, 1992 [JP] Japan ..................... 4-216631

[51] Int. Cl.$^6$ .............. C07D 205/08; C07D 413/06; C07D 403/06; C07D 417/06
[52] U.S. Cl. .............................................. 540/200
[58] Field of Search ..................................... 540/200

[56] References Cited

U.S. PATENT DOCUMENTS 5,442,055  8/1995  Iwasaki ..................... 540/200
5,550,229  8/1996  Iwasaki ..................... 540/200

FOREIGN PATENT DOCUMENTS 55-7251   1/1980  Japan .
56-142259 11/1981 Japan .

OTHER PUBLICATIONS

Mukaiyamo, Chem. Let. 1986, 915.
Abstract of Japanese Patent No. 60019764 (1985).
Abstract of JP 56–142259 (1981).
Abstract JP 55–7251 (1980).

*Primary Examiner*—Mark L. Berch
*Attorney, Agent, or Firm*—Jacobson, Price, Holman & Stern, PLLC

[57] ABSTRACT

A process for preparing 4-substituted azetidinone derivatives of the formula:

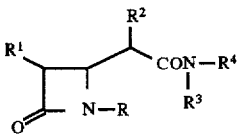

wherein R is hydrogen or an easily removable protecting group; $R^1$ is alkyl which can be substituted by hydroxy which can be protected or halogen; $R^2$ is hydrogen or alkyl; $R^3$ is alkyl, trialkylsilyl, phenyl which can be substituted by alkyl, alkoxy, nitro or halogen, cycloalkyl, naphthyl, anthracenyl, fluorenyl, benzothiazolyl or naphthalimidyl; and $R^4$ is an electron withdrawing group or can form a ring together with $R^3$, which comprises reacting an azetidinone derivative of the formula:

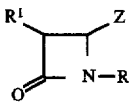

wherein R and $R^1$ are as defined above, and Z is a leaving group, and an imide compound of the formula:

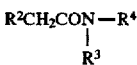

wherein $R^2$, $R^3$ and $R^4$ are as defined above, in the presence of a titanium compound of the formula:

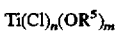

$Ti(Cl)_n(OR^5)_m$ wherein $R^5$ is lower alkyl, n and m are respectively an integer from 0 to 4, provided that n plus m always makes 4, and a base.

The process of the present invention is an industrially advantageous process using a titinium compound which is inexpensive and easy to handle. 4-Substituted azetidinone compounds prepared according to the process of the present invention can be easily hydrolyzed to a carboxylic acid which is an important intermediate for the synthesis of carbapenem compounds.

5 Claims, No Drawings

PROCESS FOR PREPARING 4-SUBSTITUTED AZETIDINONE DERIVATIVES

This application is a continuation of application Ser. No. 08/436,639, filed May 8, 1995, abandoned, which in turn is a continuation of application Ser. No. 08/108,641, filed Aug. 26, 1993, abandoned, which is a 371 of PCT/JP92/01698, filed Dec. 25, 1992.

TECHNICAL FIELD

The present invention relates to a process for preparing 4-substituted azetidinone derivatives which are important as an intermediate for the synthesis of carbapenem compounds.

BACKGROUND ART

Carboxylic acid derivatives of the formula [I']:

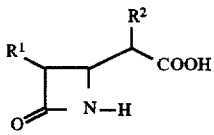

wherein $R^1$ is alkyl which can be substituted by hydroxy which can be protected or halogen and $R^2$ is hydrogen or alkyl, are important as an intermediate for the synthesis of carbapenem compounds and several processes for the preparation thereof have been proposed.

Among those processes, Jpn. Kokai Tokkyo Koho JP 87252786 discloses the process that a 4-substituted azetidinone of the formula [X']:

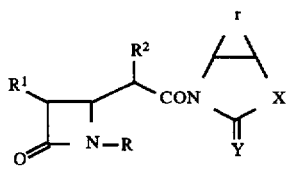

wherein $R^1$ and $R^2$ are as defined above; R is hydrogen or an easily-removable protecting group of nitrogen; r is an unsubstituted or substituted aromatic group formed together with two adjacent carbon atoms; X is oxygen, sulfur, sulfinyl, sulfonyl or $Nr^1$ group ($r^1$ is hydrogen, alkyl or phenyl); Y is oxygen, sulfur or $Nr^2$ group ($r^2$ is hydrogen, alkyl or phenyl), is easily hydrolyzed to a carboxylic acid of the general formula [I'].

Further, Tetrahedron Lett. Vol. 27, 5687–5690 (1986) discloses the compound of the formula [II"]:

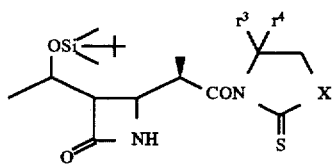

wherein X is as defined above, $r^3$ and $r^4$ are independently hydrogen or methyl.

However, these processes for preparing 4-substituted azetidinone derivatives of the formula [II'] and [II"] do not suit for industrial production because of using expensive boron triflate or tin triflate.

DISCLOSURE OF INVENTION

This invention relates to a process for preparing 4-substituted azetidinone derivatives of the formula [II]:

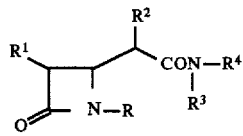

wherein R is hydrogen or an easily removable protecting group for nitrogen atom; $R^1$ is alkyl which can be substituted by hydroxy which can be protected or halogen; R2 is hydrogen or alkyl; $R^3$ is alkyl, trialkylsilyl, phenyl which can be substituted with alkyl, alkoxy, nitro or halogen, cycloalkyl, naphthyl, anthracenyl, fluorenyl, benzothiazolyl, naphthalimidyl; $R^4$ is an electron withdrawing group or can form a ring together with $R^3$, which comprises reacting an azetidinone derivative of the formula [III]:

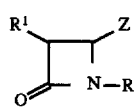

wherein R and $R^1$ are as defined above, and Z is a leaving group, with an amide compound of the formula [IV]:

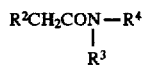

wherein $R^2$, $R^3$ and $R^4$ are as defined above, in the presence of a titanium compound of the formula [V]:

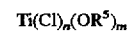

wherein $R^5$ is lower alkyl; n and m are independently an integer from 0 to 4 provided n plus m makes always 4, and a base.

As a protecting group for hydroxy at $R^1$, for example, organosilyl such as tert-butyldimethylsilyl, tert-butyldiphenylsilyl, triethylsilyl, dimethylcumylsilyl, triisopropylsilyl, dimethylhexylsilyl; oxycarbonyl such as p-nitrobenzyloxycarbonyl, p-methoxybenzyloxycarbonyl, allyloxycarbonyl; acetyl; triphenylmethyl; benzoyl and tetrahydropyranyl are examples. As a protecting group for nitrogen, for example, organosilyl as described above, benzyl, p-nitrobenzyl, p-nitrobenzoylmethyl, benzhydryl, p-methoxybenzyl and 2,4-dimethoxybenzyl are examples. As a leaving group Z, for example, acyloxy such as normal chain, branching or cyclic alkanoyloxy, monocyclic or bicyclic aroyloxy which can have hereto atoms, alkylsufonyloxy, arylsulfonyloxy, carbamoyloxy, alkoxycarboxy, aralkoxycarboxy and alkoxyalkanoyloxy; acylthio such as alkanoylthio and aroylthio; sulfinyl such as alkylsulfinyl and arylsulfinyl; sulfonyl such as alkylsulfonyl and arylsulfonyl and halogen such as fluorine, chlorine and bromine are examples.

As a base, secondary and tertiary sines, anilines and pyridine compounds are used. For example, alkylamines such as dimethylamine, diethylamine, diisopropylamine, dicyclohexylamine, diisopropylethylamine, diisopropylmethylamine, triethylamine; alkylanilines such as N-methylaniline, dimethylaniline; heterocyclic amines such as piperidine, pyrrolidine, 2,2,6,6-tetramethylpiperidine, morpholine, piperazine, 1-ethylpiperidine, 1-methylmorpholine, 1-ethylpyrrolidine, 1,4-diazabicyclo[2.2.2]octane and 1,8-diazabicyclo[5.4.0]undec-7-ene; diamine compounds such as N,N,N',N'-tetramethylethylenediamine; alkylpyridines such as α, β or γ-picoline, 2,3-, 2,4-, 2,5-, 2,6-, 3,4- or 3,5-lutidine and 2,4,6-collidine; dialkylaminopyridine such as dimethylaminopyridine and fused heterocyclized pyridines such as quinoline are examples.

As the substituent of the formula:

(hereinafter called auxiliary group), the following can be exemplified.

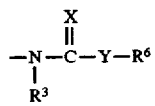

X: O, S, NH, N-alkyl, N-phenyl;

Y: O, S, sulfinyl, sulfonyl, NH, N-alkyl, N-phenyl;

$R^3$: alkyl(i—$C_3H_7$, t—$C_4H_9$), trialkylsilyl;

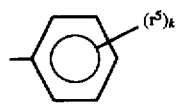

($r^5$: alkyl, halogen, alkoxy, nitro;

k: 0, 1, 2, 3, 4, 5), cycloalkyl, naphthyl,

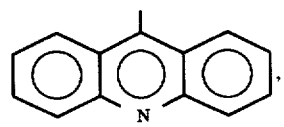

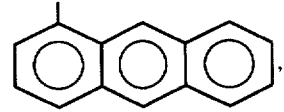

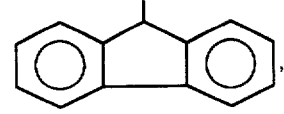

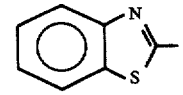

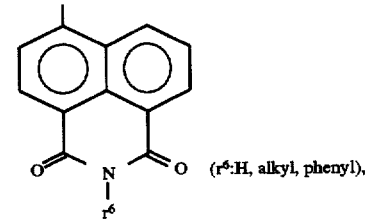

($r^6$:H, alkyl, phenyl),

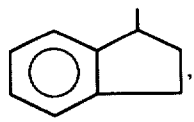

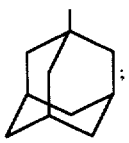

$R^6$: alkyl, haloalkyl,

($r^5$, k: as defined above), cycloalkyl, naphthyl:

2. 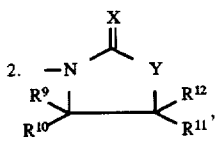

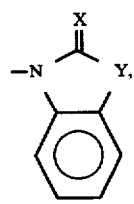

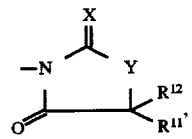

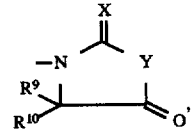

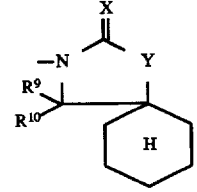

X, Y: As defined above;

$R^9$, $R^{10}$, $R^{11}$, $R^{12}$: H, alkyl,

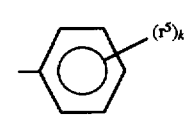

($r^5$, k: as defined above) cycloalkyl, naphthyl;

3. 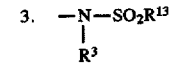

R³: As defined above; R¹³: Same as R⁶ defined above;

4. 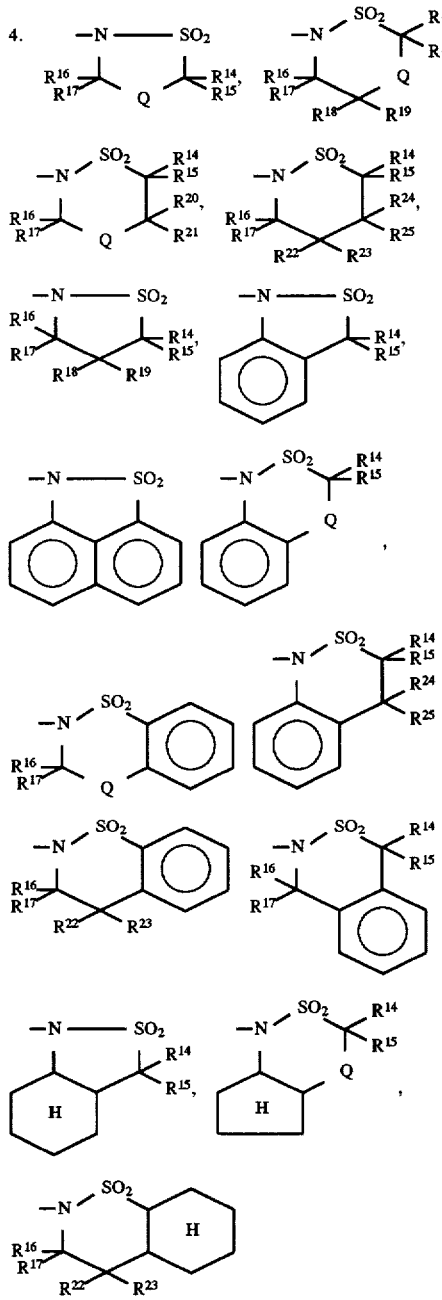

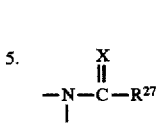

5.

R³, X: As defined above; R²⁷: Same as R⁶ defined above;

6. 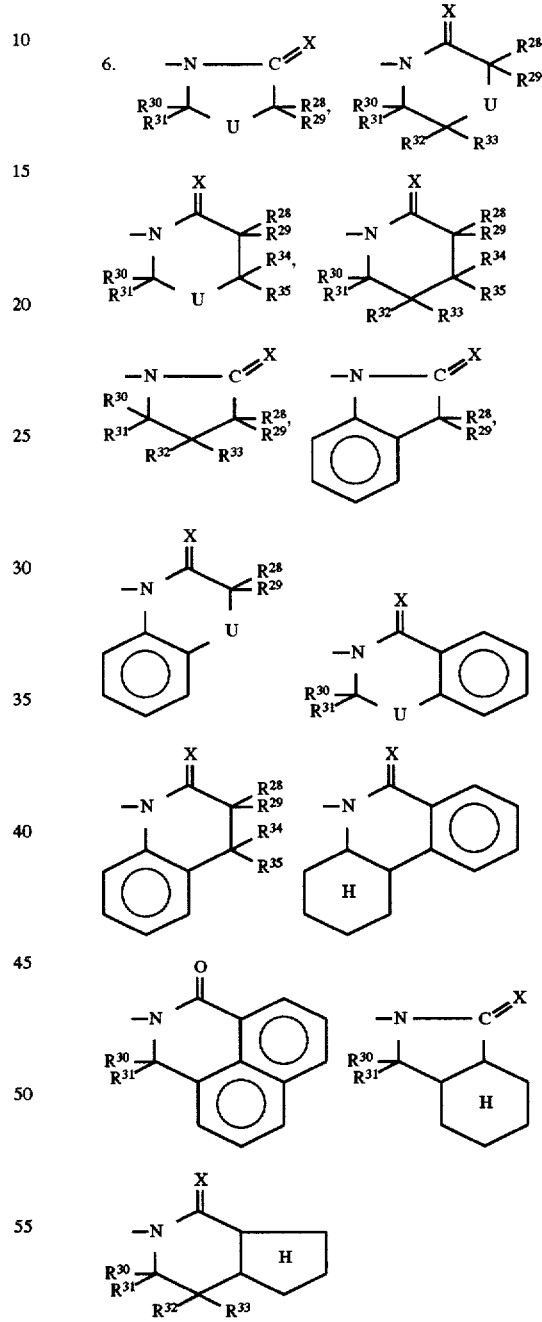

X: As defined above; U: Same as Q defined above;
R²⁸~R³⁵: Same as R¹⁴~R²⁵ defined above;

7. 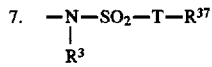

R³: As defined above;

Q: O, S, NR²⁶ (R²⁶: H, alkyl, phenyl);

R¹⁴~R²⁵: H, alkyl,

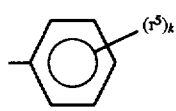

(r⁵, k: as defined above), cycloalkyl, naphthyl; R¹⁴ and R¹⁵, R¹⁶ and R¹⁷, R¹⁸ and R¹⁹, R²⁰ and R²¹, R²² and R²³ and/or R²⁴ and R²⁵ together form oxo or alkylene, respectively;

T: O, S, NR³⁸(R³⁸: H, alkyl, phenyl);

R³⁷: Same as R⁶ defined above;

8. 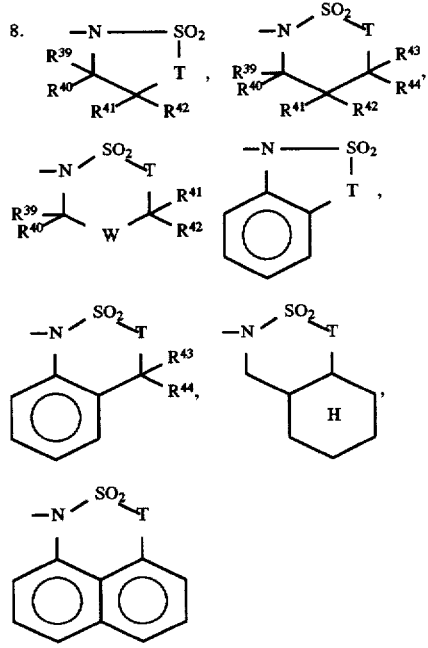

T: As defined above;
W: Same as Q defined above;
R³⁹~R⁴⁴: Same as R¹⁴~R²⁵ defined above;

9. 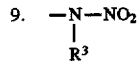

R³: As defined above;

The reaction is made firstly by reacting an amide compound of the general formula [IV] with a titanium compound of the general formula IV3, and a base such as an amine, an aniline or a pyridine compound to produce enolate in organic solvent such as chlorine-containing solvent including methylene chloride, chloroform and the like; aromatic solvent including chlorobenzene, toluene and the like; or polar solvent including acetonitrile and the like, then further reacting the resulting enolate with an azetidinone derivative of the formula [III]. The reaction temperature for both reaction of enolate formation and of the enolate and an azetidinone derivative is in the range from –50° C. to 100° C., preferably from –20° C. to 50° C.

The respective mole ratios of an amide compound of the general formula [IV], a titanium compound IV] and a base to 1 mol of azetidinone of the formula [III] in the above reaction are 1 to 8 for all.

Further, when R² is alkyl such as methyl, the ratio of α-type and β-type is influenced by the type of auxiliary group or the mole ratios of the amine and the titanium compound for the imide compound of the formula [IV]. The formation ratio of the β-type can be improved by addition of polar solvent such as DMF, THF and acetonitrile. After the completion of the reaction, the products can be isolated by usual work-up.

It is also possible to convert the products to a carboxylic acid derivative of the formula [I]:

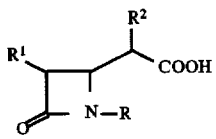

wherein R, R¹ and R² are as defined above, by direct hydrolysis without passing a process of isolation.

Best Mode for Carrying Out the Invention

The present invention is further illustrated in detail according to the following examples.

EXAMPLE 1

Preparation of β-methyl derivative (3-[(R)-2-[(3S, 4R)-3-[(R)-1-tert-butyldimethylsilyloxyethyl]-2-oxoazetidin-4-yl]propionyl]benzoxazolin-2-one)

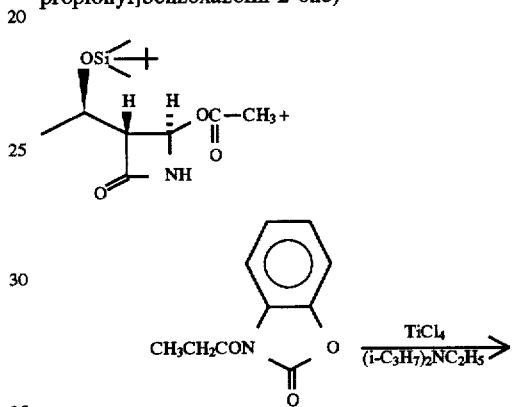

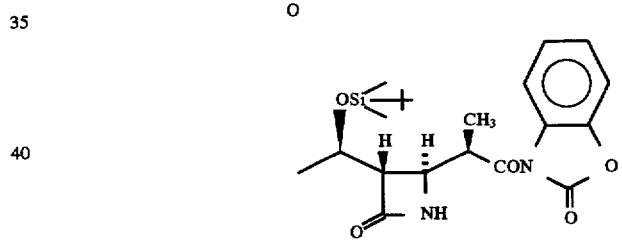

3-Propionylbenzoxazolin-2-one (189 mg, 1 mmol) solution in methylene chloride (2 ml) was cooled to –20° C. and titanium tetrachloride/methylene chloride solution (1M, 1 ml, 1 mmol) was added to the solution. After aging for 30 minutes at –20° C., N,N-diisopropylethylamine (388 mg, 3 mmol) solution in methylene chloride (1 ml) and (3R, 4R)-4-acetoxy-3-[(R)-1-tert-butyldimethylsilyloxyethyl]azetidin-2-one (287.5 mg, 1 mmol) solution in methylene chloride (1 ml) were added to the solution at the same temperature. After aging the reaction mixture for 2 hours at –20° C., it was warmed to 0° C. and 10% sodium hydrogen carbonate aq. solution (10 ml) was added under stirring. The insoluble matter was removed by filtration, the organic layer separated from the filtrate was analyzed by using HPLC. The result showed that the organic layer contained 108 mg of the β-methyl derivative (β-methyl derivative: α-methyl derivative=96:4).

EXAMPLE 2

Preparation of β-methyl derivative (3-[(R)-2-[(3S, 4R)-3-[(R)-1-tert-butyldimethylsilyloxyethyl]-2-oxoazetidin-4-yl]propionyl]-4,4-dimethyloxazolidine-2-thione)

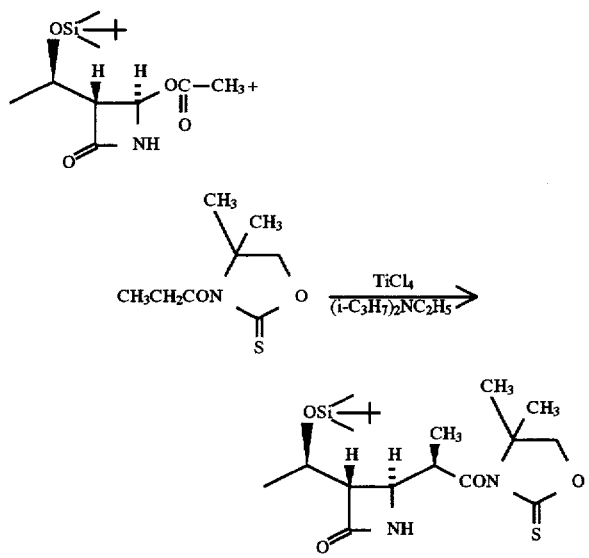

4,4-Dimethyl-3-propionyloxazolidine-2-thione (187 mg, 1 mmol) solution in methylene chloride (2 ml) was cooled to −20° C. and titanium tetrachloride/methylene chloride solution (1M, 1 ml, 1 mmol) was added to the solution. After aging for 30 minutes at −20° C., N,N-diisopropylethylamine (259 mg, 2 mmol) solution in methylene chloride (1 ml) and (3R, 4R)-4-acetoxy-3-[(R)-1-tert-butyldimethylsilyloxyethyl]azetidin-2-one (287.5 mg, 1 mmol) solution in methylene chloride (1 ml) were added to the solution at the same temperature. After aging the reaction mixture for 1 hour at −20° C., it was warmed to 20° C. and further stirred for 8 hours. The reaction mixture was then cooled to 0° C. and 10% sodium hydrogen carbonate aq. solution (10 ml) was added under stirring. The insoluble matter was removed by filtration, the organic layer separated from the filtrate was analyzed by using HPLC. The result showed that the organic layer contained 196 mg of the β-methyl derivative (β-methyl derivative: α-methyl derivative=95:5).

EXAMPLE 3

Preparation of β-methyl derivative (3-[(R)-2-[(3R, 4R)-3-[(R)-1-tert-butyldimethylsilyloxyethyl]-2-oxoazetidin-4-yl] propionyl]-4,4-dimethyloxazolidine-2-thione)

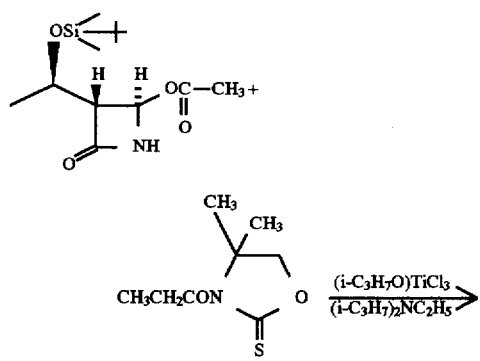

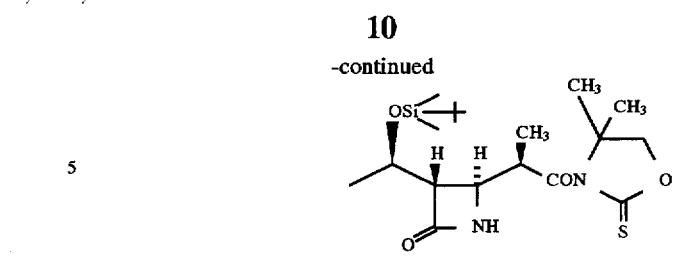

Tetraisopropoxytitanium (71 mg, 0.25 mmol) was added to titanium tetrachloride/methylene chloride solution (1M, 0.75 ml, 0.75 mmol) at room temperature, then trichloroisopropoxytitanium solution was prepared by aging the above mixture for 2 hours at the same temperature. The reaction mixture was cooled to 0° C., then 4,4-dimethyl-3-propionyloxazolidine-2-thione (187 mg, 1 mmol) solution in methylene chloride (2 ml) was added to the solution at the same temperature. After aging for 30 minutes at 0° C., N,N-diisopropylethylamine (259 mg, 2 mmol) solution in methylene chloride (1 ml) was added to the solution at the same temperature. Further aging for 30 min. at 0° C., (3R, 4R)-4-acetoxy-3-[(R)-1-tert-butyldimethylsilyloxyethyl] azetidin-2-one (287.5 mg, 1 mmol) solution in methylene chloride (1 ml) was added to the solution at the same temperature. After aging the reaction mixture for 8 hours at 0° C., it was warmed to 20° C. and further stirred for 3 hours. The reaction mixture was then cooled to 0° C. and 10% sodium hydrogen carbonate aq. solution (10 ml) was added under stirring. The insoluble matter was removed by filtration, the organic layer separated from the filtrate was analyzed by using HPLC. The result showed that the organic layer contained 118 mg of the β-methyl derivative (β-methyl derivative: α-methyl derivative=81:19).

EXAMPLE 4

Preparation of β-methyl derivative (3-[(R)-2-[(3S, 4R)-3-[(R)-1-tert-butyldimethylsilyloxyethyl]- 2-oxoazetidin-4-yl] propionyl]-4,4-dimethyloxazolidine-2-thione)

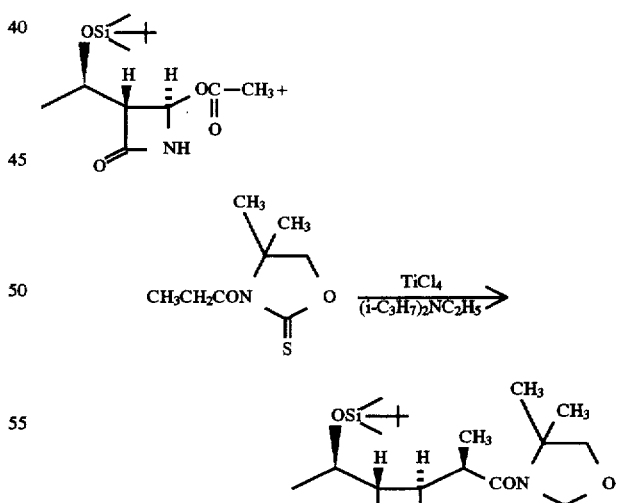

4,4-Dimethyl-3-propionyloxazolidine-2-thione (375 mg, 2 mmol) solution in methylene chloride (2 ml) was cooled to −20° C., then titanium tetrachloride/methylene chloride solution (1M, 2 ml, 2 mmol) was added to the solution. After aging for 30 minutes at −20° C., N,N-diisopropylethylamine (259 mg, 2 mmol) solution in methylene chloride (1 ml) and (3R, 4R)-4-acetoxy-3-[(R)-1-tert-butyldimethylsilyloxyethyl]azetidin-2-one (287.5 mg, 1 mmol) solution in methylene chloride (1 ml) were added to the solution at the same temperature. After aging the reaction mixture for 1 hour at −20° C., it was warmed to 20° C. and further stirred for 3 hours. The reaction mixture was then cooled to 0° C. and 10% sodium hydrogen carbonate aq. solution (10 ml) was added under stirring. The insoluble matter was removed by filtration, the organic layer separated from the filtrate was analyzed by using HPLC. The result showed that the organic layer contained 334 mg of the β-methyl derivative (β-methyl derivative: α-methyl derivative=97:3).

EXAMPLE 5

Preparation of β-methyl derivative (3-[(R)-2-[(3S, 4R)-3-[(R)-1-tert-butyldimethylsilyoxyethyl]-2-oxoazetidin-4-yl]propionyl]-4,4-dimethylthiazolidine-2-thione)

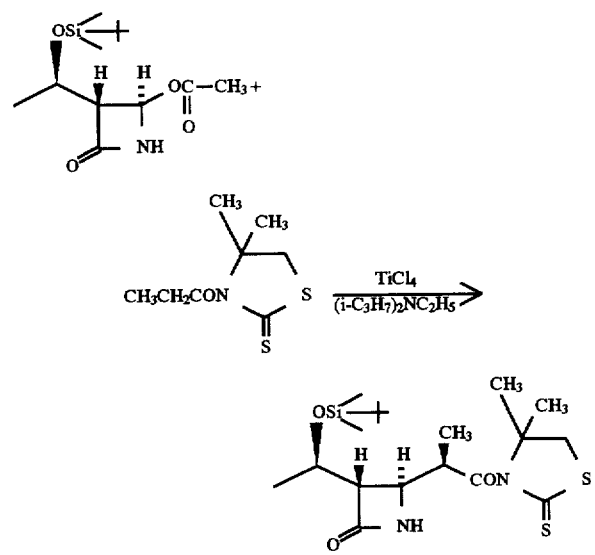

4,4-Dimethyl-3-propionylthiazolidine-2-thione (407 mg, 2 mmol) solution in methylene chloride (2 ml) was cooled to −20° C., then titanium tetrachloride/methylene chloride solution (1M, 2 ml, 2 mmol) was added to the solution. After aging for 30 minutes at −20° C., N,N-diisopropylethylamine (259 mg, 2 mmol) solution in methylene chloride (1 ml) and (3R, 4R)-4-acetoxy-3-[(R)-1-tert-butyldimethylsilyloxyethyl]azetidin-2-one (287.5 mg, 1 mmol) solution in methylene chloride (1 ml) were added to the solution at the same temperature. After aging the reaction mixture for 1 hour at −20° C., it was warmed to 20° C. and further stirred for 3 hours. The reaction mixture was then cooled to 0° C. and 10% sodium hydrogen carbonate aq. solution (10 ml) was added under stirring. The insoluble matter was removed by filtration, the organic layer separated from the filtrate was analyzed by using HPLC. The result showed that the organic layer contained 150 mg of the β-methyl derivative (β-methyl derivative: α-methyl derivative=61:39).

EXAMPLE 6

Preparation of β-methyl derivative (3-[(R)-2-[(3R, 4R)-3-[(R)-1-tert-butyldimethylsilyloxyethyl]-2-oxoazetidin-4-yl]propionyl]-4,4-dimethylthiazolidin-2-one)

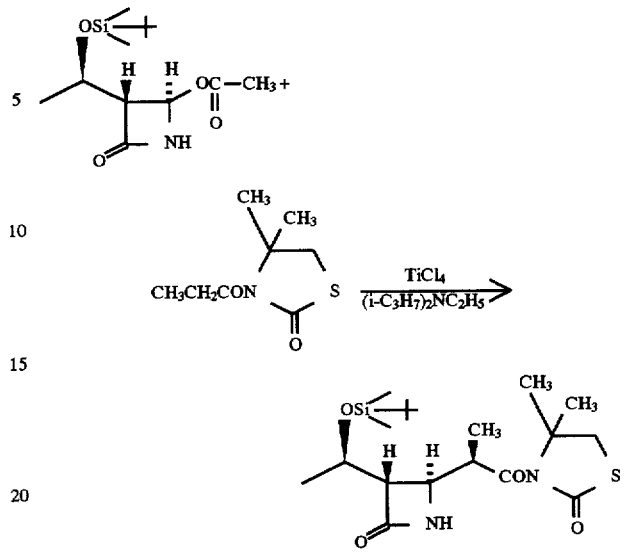

4,4-Dimethyl-3-propionylthiazolidin-2-one (375 mg, 2 mmol) solution in methylene chloride (2 ml) was cooled to −20° C., then titanium tetrachloride/methylene chloride solution (1M, 2 ml, 2 mmol) was added to the solution. After aging for 30 minutes at −20° C., N,N-diisopropylethylamine (259 mg, 2 mmol) solution in methylene chloride (1 ml) and (3R, 4R)-4-acetoxy-3-[(R)-1-tert-butyldimethylsilyloxyethyl]azetidin-2-one. (287.9 mg, 1 mmol) solution in methylene chloride (1 ml) were added to the solution at the same temperature. After aging the reaction mixture for 1 hour at −20° C., it was warmed to 20° C. and further stirred for 3 hours. The reaction mixture was then cooled to 0° C. and 10% sodium hydrogen carbonate aq. solution (10 ml) was added under stirring. The insoluble matter was removed by filtration, the organic layer separated from the filtrate was analyzed by using HPLC. The result showed that the organic layer contained 247 mg of the β-methyl derivative (β-methyl derivative: α-methyl derivative=81:19).

EXAMPLE 7

Preparation of (3-[(3S, 4R)-3-[(R)-1-tert-butyldimethylsilyloxyethyl]-2-oxoazetidin-4-yl]acetyl-4,4-dimethyloxazolidine-2-thione)

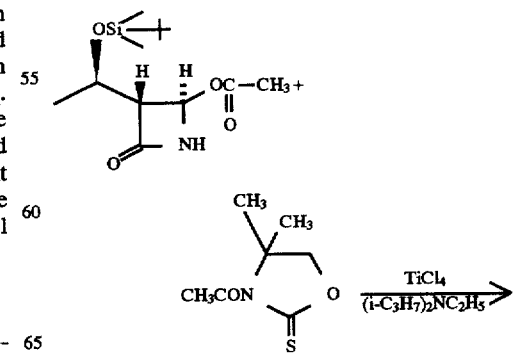

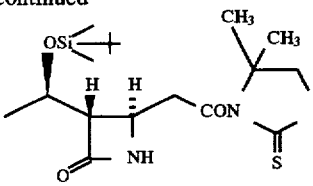

3-Acetyl-4,4-dimethyloxazolidine-2-thione (375 mg, 2 mmol) solution in methylene chloride (2 ml) was cooled to 0° C., then titanium tetrachloride/methylene chloride solution (1M, 2 ml, 2 mmol) was added to the solution. After aging for 15 minutes at 0° C., N,N-diisopropylethylamine (259 mg, 2 mmol) solution in methylene chloride (1 ml) and (3R, 4R)-4-acetoxy-3-[(R)-1-tert-butyldimethylsilyloxyethyl]azetidin-2-one (287.5 mg, 1 mmol) solution in methylene chloride (1 ml) were added to the solution at the same temperature. After aging the reaction mixture for 1 hour at 0° C., it was warmed to 20° C. and further stirred for 3 hours. The resulting mixture solution was then cooled to 0° C. and 10% sodium hydrogen carbonate aq. solution (10 ml) was added under stirring. The insoluble matter was removed by filtration, the organic layer separated from the filtrate was analyzed by using HPLC. The result showed that the organic layer contained 280 mg of the product.

EXAMPLE 8

Preparation of β-methyl derivative (3-[(R)-2-[(3S, 4R)-3-[(R)-1-tert-butyldimethylsilyloxyethyl]-2-oxoazetidin-4-yl]propionyl]-4,4-dimethyloxazolidine-2-thione)

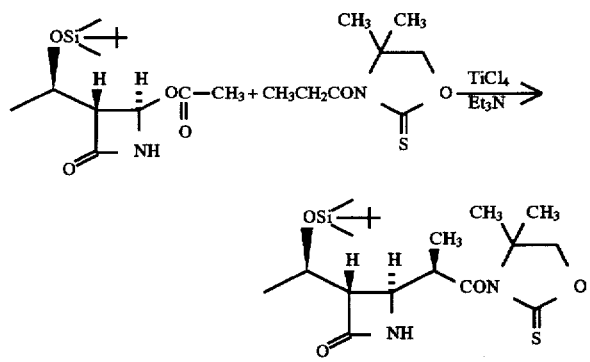

After addition of titanium tetrachloride (256 g, 1.35 mol) to 4,4-dimethyl-3-propionyloxazolidine-2-thione (243 g, 1.3 mol) solution in methylene chloride (4 l) in the temperature range from 20° to 35° C., triethylamine (126 g, 1.25 mol) and (3R, 4R)-4-acetoxy-3-[(R)-1-tert-butyldimethylsilyloxyethyl]azetidin-2-one (287.5 g, 1 mol) were added to the mixture at the same temperature. After aging the reaction mixture for 0.5 hour under reflux, it was cooled to 0° C. and added to Water at the same temperature under stirring, then stirred for 0.5 hour under the same temperature. The organic layer was separated and analyzed by using HPLC. The result showed that the organic layer contained 323 g of the β-methyl derivative (β-methyl derivative: α-methyl derivative=97:3). The organic layer was washed with water (1l) and added with Isoper G® (Exxon Chemical)(4 l), then the organic layer was concentrated so as to be 8.6 Kg in total weight under reduced pressure. The concentrate was cooled to 5° C. under stirring and further stirred for 0.5 hour at the same temperature. The crystals deposited were taken out by filtration and dried, affording 307 g of the β-methyl derivative (β-methyl derivative: α-methyl derivative=98.5:1.5).

EXAMPLE 9

Preparation of β-methyl derivative (3-[(R)-2-[(3S, 4R)-3-[(R)-1-tert-butyldimethylsilyloxyethyl]-2-oxoazetidin-4-yl]propionyl]oxazolidine-2-thione)

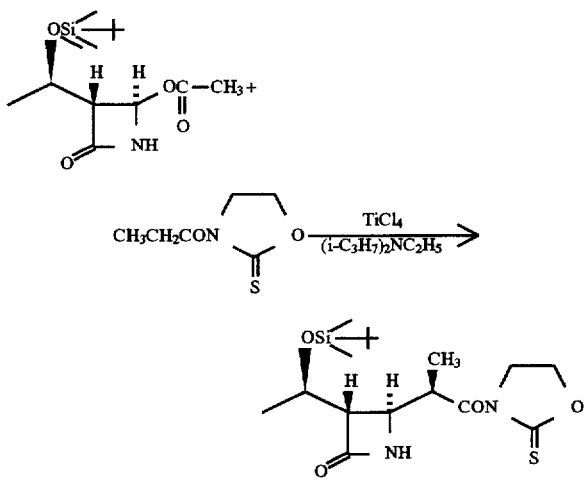

3-Propionyloxazolidine-2-thione (320 mg, 2 mmol) solution in methylene chloride (2 ml) was cooled to 0° C., then titanium tetrachloride/methylene chloride solution (1M, 2 ml, 2 mmol) was added to the solution. After aging for 15 minutes at 0° C., N,N-diisopropylethylamine (259 mg, 2 mmol) solution in methylene chloride (1 ml) and (3R, 4R)-4-acetoxy-3-[(R)-1-tert-butyldimethylsilyloxyethyl azetidin-2-one (287.5 mg, 1 mmol) solution in methylene chloride (1 ml) were added to the solution at the same temperature. After aging the reaction fixture for 1 hour at 0° C., it was warmed to 20° C. and further stirred for 3 hours. The reaction fixture was then cooled to 0° C. and 10% sodium hydrogen carbonate aq. solution (10 ml) was added under stirring. The insoluble matter was removed by filtration, the organic layer separated from the filtrate was analyzed by using HPLC. The result showed that the organic layer contained 58 mg of the β-methyl derivative (β-methyl derivative methyl derivative=65:35).

EXAMPLE 10

Preparation of α-methyl derivative (3-[(S)-2-[(3S, 4R)-3-[(R)-1-tert-butyldimethylsilyloxyethyl]-2-oxoazetidin-4-yl]propionyl]-4,4-dimethyloxazolidin-2-one)

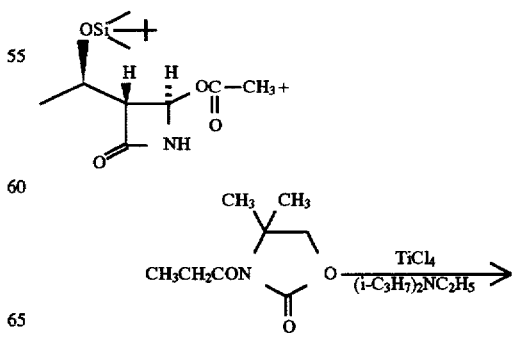

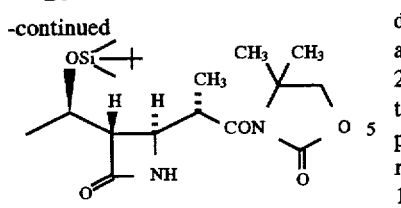

4,4-Dimethyl-3-propionyloxazolidin-2-one (342 mg, 2 mmol) solution in methylene chloride (2 ml) was cooled to −20° C., then titanium tetrachloride/methylene chloride solution (1M, 2 ml, 2 mmol) was added to the solution. After aging for 30 min. at −20° C., N, N-diisopropylethylamine (259 mg, 2 mmol) solution in methylene chloride (1 ml) and (3R, 4R)-4-acetoxy-3-[(R)-1-tert-butyldimethylsilyloxyethyl]azetidin-2-one (287.5 mg, 1 mmol) solution in methylene chloride (1 ml) were added to the solution at the same temperature. After aging the reaction mixture for 1 hour at −20° C., it was warmed to 20° C. and further stirred for 3 hours. The reaction mixture was then cooled to 0° C. and 10% sodium hydrogen carbonate aq. solution (10 ml) was added under stirring. The insoluble matter was removed by filtration, the organic layer separated from the filtrate was analyzed by using HPLC. The result showed that the organic layer contained 180 mg of the α-methyl derivative (α-methyl derivative: β-methyl derivative=68:32).

EXAMPLE 11

Preparation of α-methyl derivative (3-[(S)-2-[(3R, 4R)-3-[(R)-1-tert-butyldimethylsilyloxyethyl]-2-oxoazetidin-4-yl]propionyl]benzoxazolin-2-one)

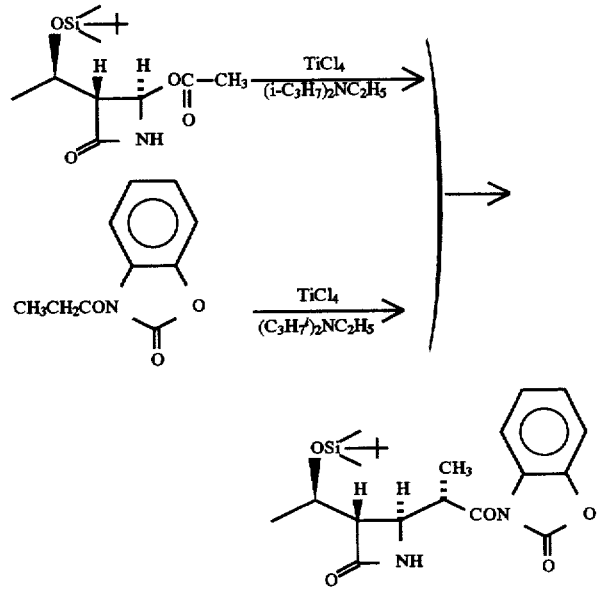

The solution of 3-propionylbenzoxazolin-2-one (3.16 g, 16.5 mmol) and N,N-diisopropylethylamine (4.27 g, 33 mmol) in methylene chloride (20 ml) was cooled to −5° C., then titanium tetrachloride (3.13 g, 16.5 mmol) solution in methylene chloride (5 ml) was added to the mixture and the reaction mixture was stirred for 15 min. at the same temperature to prepare titanium enolate solution. Besides, titanium tetrachloride (3.13 g, 16.5 mmol) solution in methylene chloride (15 ml) was cooled to −5° C., then the methylene chloride solutions of both N,N-diisopropylethylamine (0.1 g, 0.8 mmol) and (3R, 4R)-4-acetoxy-3-[(R)-1-tert-butyldimethylsilyloxyethyl]azetidin-2-one (4.31 g, 15 mmol) were added thereto at the same temperature. Then the titanium enolate solution previously prepared was added to the resulting mixture and the reaction mixture was stirred for 5 hours at the same temperature, then 10% sodium hydrogen carbonate aq. solution (100 ml) was added under stirring. The insoluble matter was removed by filtration, the organic layer separated from the filtrate was analyzed by using HPLC. The result showed that the organic layer contained 3.45 g of the α-methyl derivative (α-methyl derivative: β-methyl derivative=92:8).

EXAMPLE 12

Preparation of β-methyl derivative (3-[(R)-2-[(3S, 4R)-3-[(R)-1-tert-butyldimethylsilyloxyethyl]-2-oxoazetidin-4-yl]propionyl]-4,4-diethyloxazolidine-2-thione)

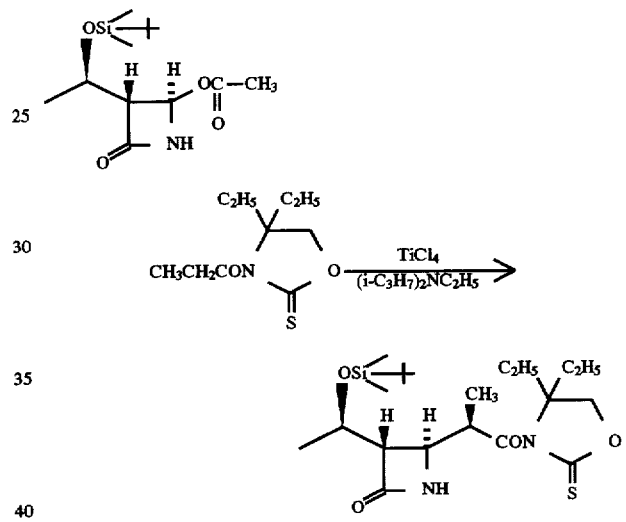

4,4-Diethyl-3-propionyloxazolidine-2-thione (431 mg, 2 mmol) solution in methylene chloride (2 ml) was cooled to 0° C., then titanium tetrachloride/methylene chloride solution (1M, 2 ml, 2 mmol) was added to the solution. After aging for 15 min. at 0° C., N,N-diisopropylethylamine (259 mg, 2 mmol) solution in methylene chloride (1 ml) and (3R, 4R)-4-acetoxy-3-[(R)-1-tert-butyldimethylsilyloxyethyl]azetidin-2-one (287.5 mg, 1 mmol) solution in methylene chloride (1 ml) were added to the mixture at the same temperature. After aging the reaction mixture for 1 hour at 0° C., it was warmed to 20° C. and further stirred for 3 hours. The reaction mixture was then cooled to 0° C. and 10% sodium hydrogen carbonate aq. solution (10 ml) was added under stirring. The insoluble matter was removed by filtration, the organic layer separated from the filtrate was analyzed by using HPLC. The result showed that the organic layer contained 332 mg of the β-methyl derivative (β-methyl derivative: α-methyl derivative=96:4).

EXAMPLE 13

Preparation of β-methyl derivative (3-[(R)-2-[(3S, 4R)-3-[(R)-1-tert-butyldimethylsilyloxyethyl]-2-oxoazetidin-4-yl]propionyl]-(S)-4-isopropyloxazoiidino-2-thione)

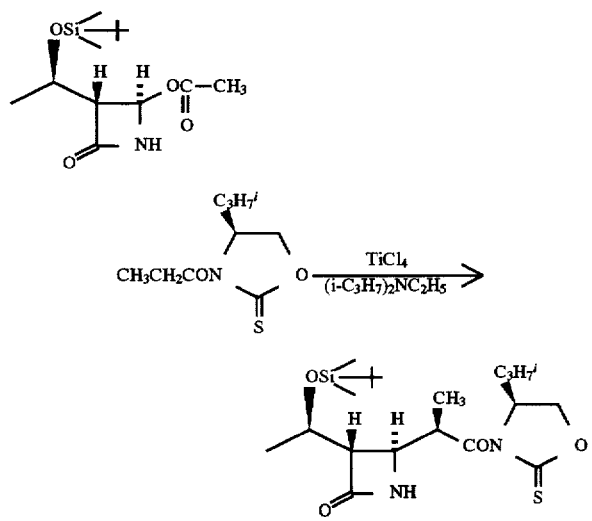

(S)-4-Isopropyl-3-proplonyloxazolidine-2-thione (402 mg, 2 mmol) solution in methylene chloride (2 ml) was cooled to 0° C., then titanium tetrachloride/methylene chloride solution (1M, 2 ml, 2 mmol) was added to the solution. After aging for 15 min. at 0° C., N,N-diisopropylethylamine (259 mg, 2 mmol) solution in methylene chloride (1 ml) and (3R, 4R)-4-acetoxy-3-[(R)-1-tert-butyldimethylsilyloxyethyl]azetidin-2-one (287.5 mg, 1 mmol) solution in methylene chloride (1 ml) were added to the mixture at the same temperature. After aging the reaction mixture for 1 hour at 0° C., it was warmed to 20° C. and further stirred for 3 hours. The reaction mixture was then cooled to 0° C. and 10% sodium hydrogen carbonate aq. solution (10 ml) was added under stirring. The insoluble matter was removed by filtration, the organic layer separated from the filtrate was analyzed by using HPLC. The result showed that the organic layer contained 203 mg of the β-methyl derivative (β-methyl derivative: α-methyl derivative=100:0).

EXAMPLE 14

Preparation of β-methyl derivative (3-[(R)-2-[(3S, 4R)-3-[(R)-1-tert-butyldimethlsilyloxyethyl]-2-oxoazetidin-4-yl]propionyl]-4,4-dibutyl-5,5-pentamethyleneoxazolidine-2-thione)

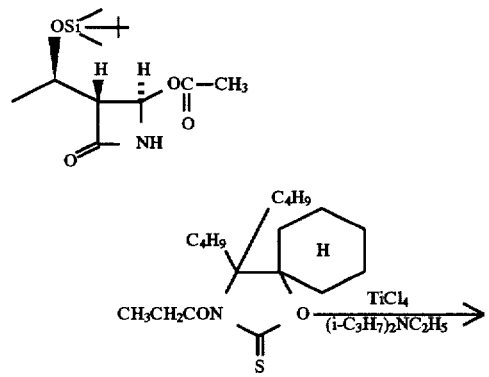

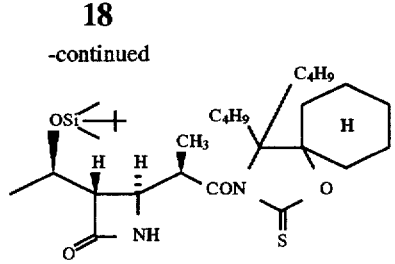

4,4-Dibutyl-5,5-pentamethylene-3-propionyloxazolidine-2-thione (678 mg, 2 mmol) solution in methylene chloride (2 ml) was cooled to -10° C., then titanium tetrachloride/methylene chloride solution (1M, 2 ml, 2 mmol) was added to the solution. After aging for 15 min. at -10° C., N, N-diisopropylethylamine (259 mg, 2 mmol) solution in methylene chloride (1 ml) and (3R, 4R)-4-acetoxy-3-[(R)-1-tert-butyldimethylsilyloxyethyl]azetidin-2-one (287.5 mg, 1 mmol) solution in methylene chloride (1 ml) were added to the mixture at the same temperature. After aging the reaction mixture for 1 hour at 0° C., it was warmed to the reflux temperature and further stirred for 3 hours. The reaction mixture was then cooled to 0° C. and 10% sodium hydrogen carbonate aq. solution (10 ml) was added under stirring. The insoluble matter was removed by filtration, the organic layer separated from the filtrate was analyzed by using HPLC. The result showed that the organic layer contained 334 mg of the β-methyl derivative (β-methyl derivative: α-methyl derivative=100:0).

EXAMPLE 15

Preparation of α-methyl derivative (1-[(S)-2-[(3S, 4R)-3-[(R)-1-tert-butyldimethylsilyloxyethyl]-2-oxoazetidin-4-yl]propionyl]-3,5,5-trimethylimidazolidine-2,4-dione)

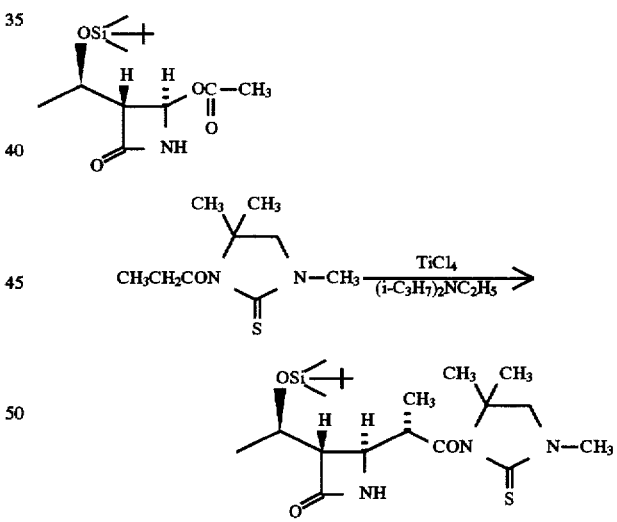

1-Propionyl-3,5,5-trimethylimidazolidine-2,4-dione (397 mg, 2 mmol) solution in methylene chloride (2 ml) was cooled to 0° C., then titanium tetrachloride/methylene chloride solution (1M, 2 ml, 2 mmol) was added to the solution. After aging for 15 min. at 0° C., N,N-diisopropylethylamine (259 mg, 2 mmol) solution in methylene chloride (1 ml) and (3R, 4R)-4-acetoxy-3-[(R)-1-tert-butyldimethylsilyloxyethyl]azetidin-2-one (287.5 mg, 1 mmol) solution in methylene chloride (1 ml) were added to the mixture at the same temperature. After aging the reaction mixture for 1 hour at 0° C., it was warmed to 20° C. and further stirred for 3 hours. The reaction mixture was then cooled to 0° C. and 10% sodium hydrogen carbonate aq. solution (10 ml) was added under stirring. The insoluble matter was removed by filtration, the organic layer separated from the filtrate was analyzed by using HPLC. The result showed that the organic layer contained 190 mg of the α-methyl derivative (α-methyl derivative: β-methyl derivative=92:8).

$^1$H NMR (270 MHz, CDCl$_3$) δ of α-methyl derivative: 0.08(6H, s), 0.89(9H, s), 1.23(3H, d), 1.26(3H, d), 1.67(3H, s), 1.67(3H, s), 2.81(1H, dd), 3.09(3H, s), 3.6–4.3 (3H, m), 5.99(1H, s).

EXAMPLE 16

Preparation of β-methyl derivative (methyl N-[(R)-2-[(3S, 4R)-3-[(R)-1-tert-butyldimethylsilyloxyethyl]-2-oxoazetidin-4-yl]propionyl]-N-methylthiocarbamate)

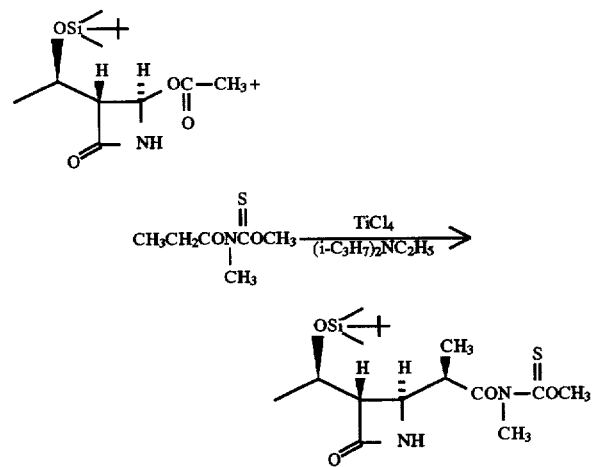

Methyl N-methyl-N-propionylthiocarbamate (1.61 g, 10 mmol) solution in methylene chloride (30 ml) was cooled to 0° C., then titanium tetrachloride (1.9 g, 10 mmol) solution in methylene chloride (5 ml) was added to the solution. After aging for 15 min. at 0° C., N,N-diisopropylethylamine (1.3 g, 10 mmol) solution in methylene chloride (5 ml) and (3R, 4g)-4-acetoxy-3-[(g)-1-tert-butyldimethylsilyloxyethyl] azetidin-2-one (1.44 g, 5 mmol) solution in methylene chloride (10 ml) were added to the mixture at the same temperature. After aging the reaction mixture for 1 hour at 0° C., it was warmed to 20° C. and further stirred for 3 hours. The reaction mixture was then cooled to 0° C. and 10% sodium hydrogen carbonate aq. solution (50 ml) was added thereto under stirring. The insoluble matter was removed by filtration, the organic layer separated from the filtrate was analyzed by using HPLC. The result showed that the organic layer contained 1.35 g of the β-methyl derivative (β-methyl derivative: α-methyl derivative=87:13). The organic layer was concentrated and purified by using silica gel column chromatography, affording the purified β-methyl derivative.

The melting point of the β-methyl derivative: 156°–157° C.

EXAMPLE 17

Preparation of β-methyl derivative (methyl N-tert-butyl-N-[(R)-2-[(3S, 4R)-3-[(R)-1-tert-butyldimethylsilyloxyethyl]-2-oxoazetidin-4-yl]propionyl]thiocarbamate)

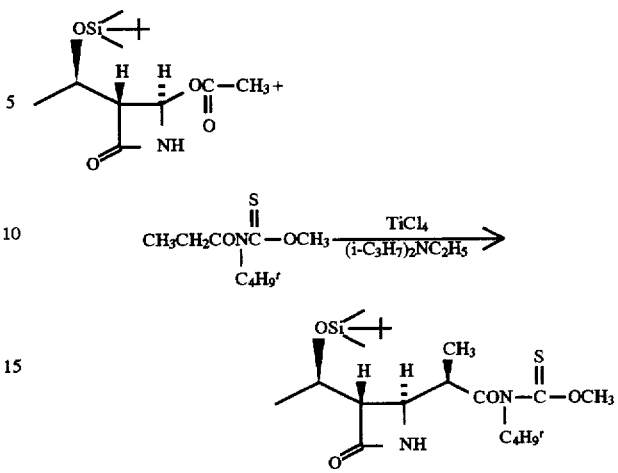

Methyl N-tert-butyl-N-propionylthiocarbamate (1.0 g, 4.9 mmol) solution in methylene chloride (30 ml) was cooled to 0° C., then titanium tetrachloride (0.93 g, 4.9 mmol), solution in methylene chloride (5 ml) was added to the solution. After aging for 15 min. at 0° C., N,N-diisopropylethylamine (0.64 g, 4.9 mmol) solution in methylene chloride (5 ml) and (3R, 4R)-4-acetoxy-3-[(R)-1-tert-butyldimethylsilyloxyethyl]azetidin-2-one (0.71 g, 2.5 mmol) solution in methylene chloride (10 ml) were added to the mixture at the same temperature. After aging the reaction mixture for 1 hour at 0° C., it was warmed to 20° C. and further stirred for 3 hours. The reaction mixture was then cooled to 0° C. and 10% sodium hydrogen carbonate aq. solution (50 ml) was added thereto under stirring. The insoluble matter was removed by filtration, the organic layer separated from the filtrate was analyzed by using HPLC. The result showed that the organic layer contained 0.38 g of the β-methyl derivative (β-methyl derivative: α-methyl derivative=100:0). It was purified according to the method described in Example 16, affording the purified fi-methyl derivative.

The melting point of the β-methyl derivative: 128°–129° C.

EXAMPLE 18

Preparation of β-methyl derivative (methyl N-[(R)-2-[(4S, 4R)-3-[(R)-1-tert-butyldimethylsilyloxyethyl]-2-oxoazetidin-4-yl]propionyl]-N-phenylthiocarbamate)

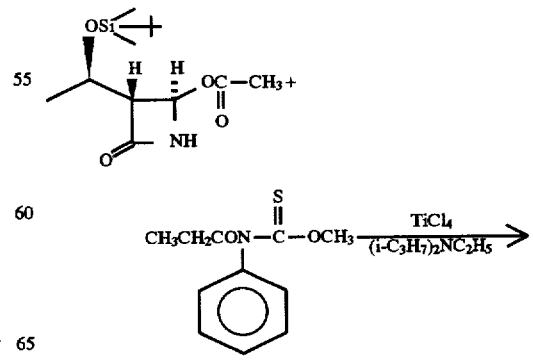

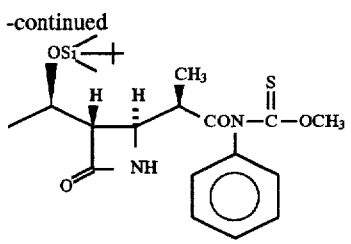

Methyl N-phenyl-N-propionylthiocarbamate (2.23 g, 10 mmol) solution in methylene chloride (30 ml) was cooled to 0° C., then titanium tetrachloride (1.9 g, 10 mmol) solution in methylene chloride (5 ml) was added to the solution. After aging for 15 min. at 0° C., N,N-diisopropylethylamine (1.3 g, 10 mmol) solution in methylene chloride (5 ml) and (3R, 4R)-4-acetoxy-3-[(R)-1-tert-butyldimethylsilyloxyethyl]azetidin-2-one (1.44 g, 5 mmol) solution in methylene chloride (10 ml) were added to the mixture at the same temperature. After aging the reaction mixture for 1 hour at 0° C., it was warmed to 20° C. and further stirred for 3 hours. The reaction mixture was then cooled sodium hydrogen carbonate aq. solution (50 ml) was added thereto under stirring. The insoluble matter was removed by filtration, the organic layer separated from the filtrate was analyzed by using HPLC. The result showed that the organic layer contained 1.16 g of the β-methyl derivative (β-methyl derivative: α-methyl derivative=72:28). It was purified according to the method described in Example 16, affording the purified β-methyl derivative. The melting point of the β-methyl derivative: 100°~101° C.

EXAMPLE 19

Preparation of a-methyl derivative (N-[(S)-2-[(3S, 4R)-3-[(R)-1-tert-butyldimethylsilyloxyethyl]-2-oxoazetidin-4-yl]propionyl]-N-(4-chlorophenyl)-p-toluenesulfonamide)

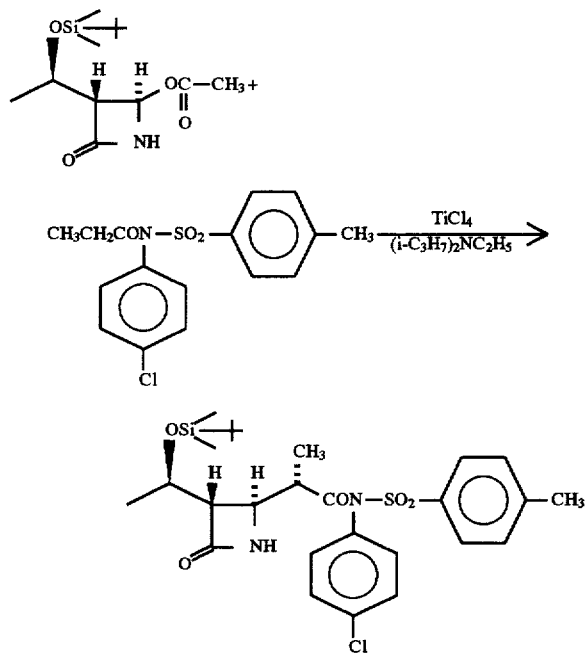

N-(4-chlorophenyl)-N-propionyl-p-toluenesulfonamide (676 mg, 2 mmol) solution in methylene chloride (2 ml) was cooled to 0° C., then titanium tetrachloride/methylene chloride (1M, 2 ml, 2 mmol) solution was added to the solution. After aging for 15 min. at 0° C., N,N-diisopropylethylamine (259 mg, 2 mmol) solution in methylene chloride (1 ml) and (3R, 4R)-4-acetoxy-3-[(R)-1-tert-butyldimethylsilyloxyethyl]azetidin-2-one (287.5 mg, 1 mmol) solution in methylene chloride (1 ml) were added to the solution at the same temperature. After aging the reaction mixture for 1 hour at 0° C., it was warmed to 20° C. and further stirred for 3 hours. The reaction mixture was then cooled to 0° C. and 10% sodium hydrogen carbonate aq. solution (10 ml) was added thereto under stirring. The insoluble matter was removed by filtration, the organic layer separated from the filtrate was analyzed by using HPLC. The result showed that the organic layer contained 190 mg of the α-methyl derivative (α-methyl derivative: β-methyl derivative=59:41). It was purified according to the method described in Example 16, affording the purified α-methyl derivative.

¹H NMR (270 MHz, CDCl₃) δ of a α-methyl derivative: 0.03(6H, d), 0.84(9H, s), 1.01(3H, d), 1.14(3H, d), 2.2~2.6 (8H, m), 7.1~7.9(8H, m), 3.65~3.78(1H, m), 4.0~4.15(1H, m), 5.90(1H, s)

EXAMPLE 20

Preparation of α-methyl derivative (N-(8)-2-[(3S, 4R)-3-[(R)- 1-tert-butyldimethylsilyloxyethyl]-2-oxoazetidin-4-yl] propionyl]-N-isopropylbenzamide)

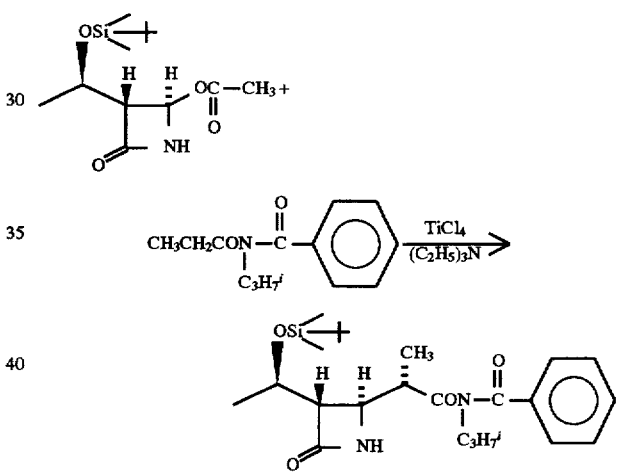

Titanium tetrachloride (0.43 g, 2.3 mmol) solution in methylene chloride (5 ml) was added to N-isopropyl-N-propionylbenzamide (0.5 g, 2.3 mmol) solution in methylene chloride (10 ml) at room temperature, then triethylamine (0.22 g, 2.1 mmol) and (3R, 4R)-4-acetoxy-3-[(R)-1-tert-butyldimethylsilyloxyethyl]azetidin-2-one (0.44 g, 1.52 mmol) were added to the mixture at the same temperature. The reaction mixture was stirred for i hour at 20° C., then cooled to 0° C. and added with 10% sodium hydrogen carbonate aq. solution (50 ml) under stirring. The insoluble matter was removed by filtration, the organic layer separated from the filtrate was analyzed by using HPLC. The result showed that the organic layer contained 0.25 g of the a-methyl derivative (α-methyl derivative: β-methyl derivative=95:5). It was purified according to the method described in Example 16, affording the purified α-methyl derivative.

¹H NMR (270 MHz, CDCl₃) δ of the α-methyl derivative: 0.06(6H, s), 0.87(9H, s), 0.99(3H, d), 1.06(3H, d), 1.38(6H, d), 2.6~2.7(1H, m), 2.83(1H, dd), 3.76~3.82 (1H, m), 4.05~4.18 (1H, m), 4.45~4.66(1H, m), 6.16(1H, s) 7.3~7.8 (5H, m)

EXAMPLE 21

Preparation of β-methyl derivative (N-[(R)-2[(3S, 4R)-3[(R)-1-tert-butyldimethylsilyloxyethyl]-2-oxoazetidin-4-yl]propionyl]-N-isopropyl-p-toluenesulfonamide)

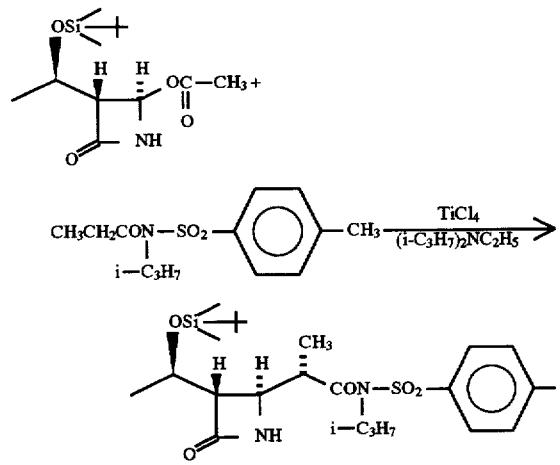

N-isopropyl-N-propionyl-p-toluenesulfonamide (2.69 g, 10 mmol) solution in methylene chloride (20 ml) was cooled to 0° C., then titanium tetrachloride (1.9 g, 10 mmol) solution in methylene chloride (2.5 ml) was added to the solution. After aging for 1 hour at 0° C. N,N-diisopropylethylamine (1.29 g, 10 mmol) solution in methylene chloride (2.5 ml) and (3R, 4R)-4-acetoxy-3-[(R)-1-tert-butyldimethylsilyloxyethyl]azetidin-2-one (1.44 g, 5 mmol) solution in methylene chloride (5 ml) were added to the mixture at the serge temperature. After aging the reaction mixture for 2 hour at 0° C., it was warmed to 20° C. and further stirred for 3 hours. The reaction mixture was then cooled to 0° C. and 10% sodium hydrogen carbonate aq. solution (50 ml) was added thereto under stirring. The insoluble matter was removed by filtration and the filtrate was washed with water. The filtrate was dried with anhydrous magnesium sulfate, then concentrated under reduced pressure. The residue was purified by silica gel chromatography, affording 1.5 g of the mixture of the β-methyl derivative and the α-methyl derivative. From the analytical result of NMR ($^1$H), the ratio of the β-methyl derivative and the α-methyl derivative was 67: 33. $^1$H NMR (270 MHz, CDCl$_3$) δ of a methyl derivative: 7.76(d, 2H), 7.38(d, 2H), 6.00(br S, 1H), 4.55(m, 1H), 4.15(m, 1H), 3.83(q, 1H), 3.59(m, 1H), 2.89(br S, 1H), 1.43(q, 6H), 1.11(d, 3H), 1.01(S, 3H), 0.87(S, 9H), 0.06(S, 6H)

Industrial Applicability

The process of the present invention is an industrially advantageous process using titanium compounds of the general formula [V] which are inexpensive and can be remored easily as titanium oxides.

Further, when R$^2$ is alkyl such as methyl group, it is possible to obtain the β-type derivatives selectivly, which are important as intermediates for the synthesis of carbapenem compounds, by adjusting the mole ratios or optionally selecting an auxiliary group.

We claim:

1. A process for preparing 4-substituted azetidinone derivatives of the formula:

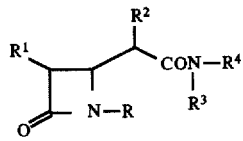

wherein R is hydrogen or an easily removable protecting group for nitrogen, R$^1$ is alkyl which can be substituted by hydroxy which can be protected or halogen, R$^2$ is hydrogen or alkyl, R$^3$ is alkyl, trialkylsilyl, phenyl which can be substituted by alkyl, alkoxy, nitro or halogen, cycloalkyl, naphthyl, anthracenyl, fluorenyl, benzothiazolyl or naphthalimidyl and R$^4$ is an electron withdrawing group selected from a group consisting of —C(=X)Y—R$^6$, —SO$_2$R$^{13}$, —C(=X)—R$^{27}$ and —SO$_2$—T—R$^{37}$ or forms a ring together with nitrogen and R$^3$, wherein when R$^4$ is

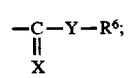

X is oxygen, sulfur or NR$^7$; R$^7$ is hydrogen, alkyl or phenyl; Y is oxygen, sulfur, sulfinyl, sulfonyl or NR$^8$; wherein R$^8$ is hydrogen, alkyl or phenyl; and R$^6$ is alkyl; phenyl which can be substituted by alkyl, alkoxy, nitro or halogen; cycloalkyl, or naphthyl, or R$^6$ together with —C(=X)Y forms a 5-membered ring together with NR$^3$ of the formula:

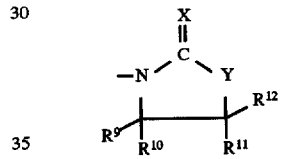

wherein R$^9$, R$^{10}$, R$^{11}$ and R$^{12}$ are independently hydrogen; alkyl; phenyl which can be substituted by lower alkyl, alkoxy, nitro or halogen; cycloalkyl; or naphthyl; or R$^9$ and R$^{10}$ or R$^{11}$ and R$^{12}$ can respectively form an oxo or alkylene group; or a benzene ring formed together with R$^9$, R$^{10}$, R$^{11}$ and R$^{12}$ and two adjacent carbon atoms connecting these substituents;

when R$^4$ is —SO$_2$R$^{13}$; R$^{13}$ is alkyl; haloalkyl; phenyl which can be substituted by alkyl, alkoxy, nitro or halogen; cycloalkyl or naphthyl, or R$^{13}$ together with SO$_2$ forms a 5- or 6-membered ring together with NR$^3$ selected from the group consisting of the formulas:

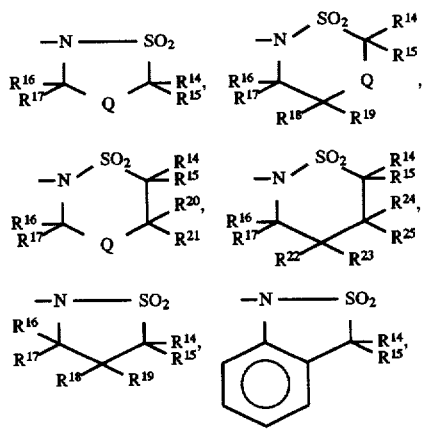

-continued

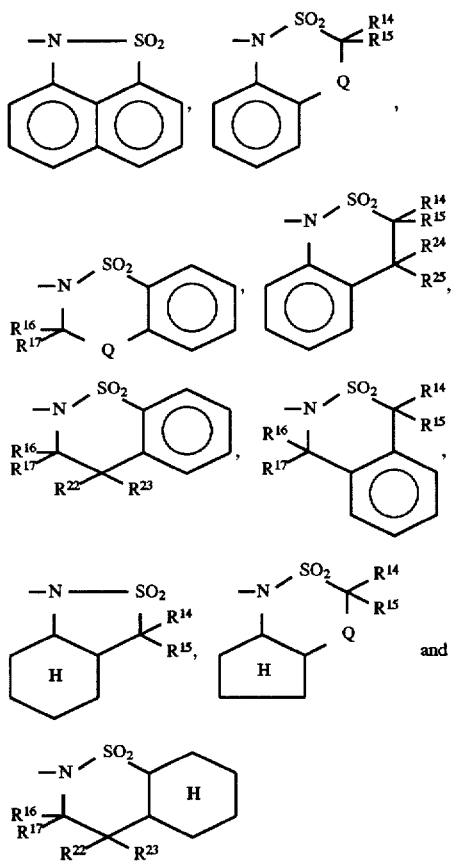

wherein $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ are independently hydrogen; alkyl; phenyl which can be substituted by alkyl, alkoxy, nitro or halogen; or cycloalkyl; or $R^{14}$ and $R^{15}$, $R^{16}$ and $R^{17}$, $R^{18}$ and $R^{19}$, $R^{20}$ and $R^{21}$, $R^{22}$ and $R^{23}$, or $R^{24}$ and $R^{25}$ can respectively form an oxo or alkylene group; Q is O, S or $NR^{26}$ wherein $R^{26}$ is hydrogen, alkyl or phenyl;

when $R^4$ is

wherein X is as defined above, $R^{27}$ is alkyl; haloalkyl; phenyl which can be substituted by alkyl, alkoxy, nitro or halogen; cycloalkyl or naphthyl, or $R^{27}$ together with C(=X) forms a 5- or 6-membered ring together with $NR^3$ selected from the group consisting of the formulas:

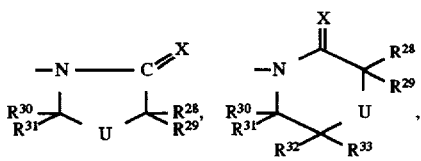

-continued

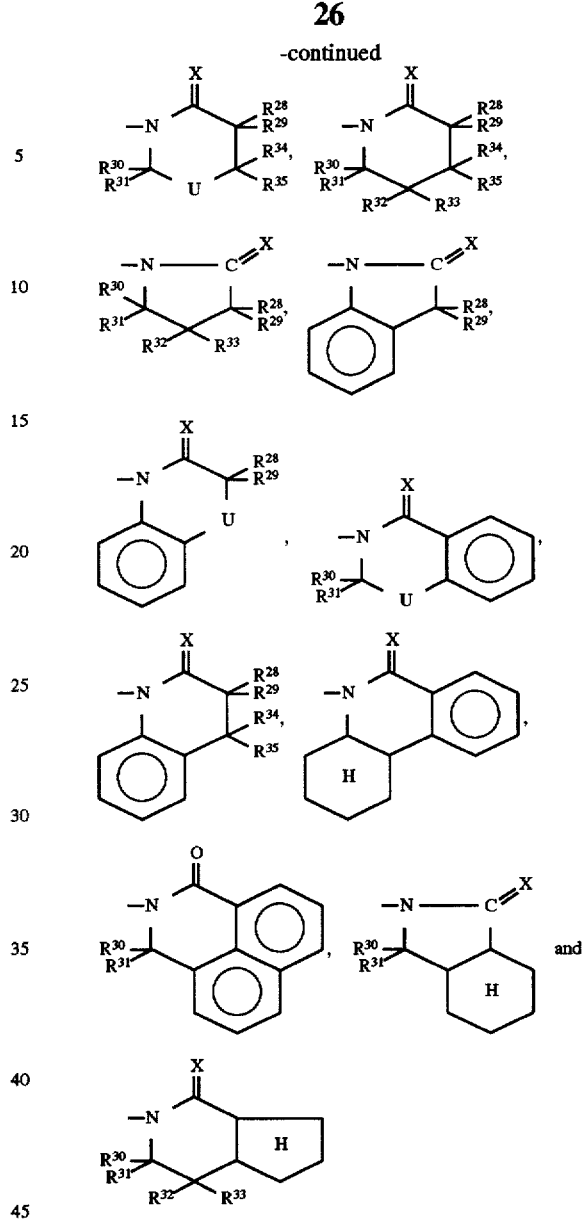

wherein X is as defined above; $R^{28}$, $R^{29}$, $R^{30}$, $R^{31}$, $R^{32}$, $R^{33}$, $R^{34}$ and $R^{35}$ are independently hydrogen; alkyl; phenyl which can be substituted by alkyl, alkoxy, nitro or halogen; cycloalkyl or naphthyl; or $R^{28}$ and $R^{29}$, $R^{30}$ and $R^{31}$, $R^{32}$ and $R^{33}$ or $R^{34}$ and $R^{35}$ can respectively form an oxo or alkylene group; and U is O, S or $NR^{36}$ wherein $R^{36}$ is hydrogen, alkyl or phenyl; and when $R^4$ is $SO_2$—T—$R^{37}$ T is O, S or $NR^{38}$; wherein $R^{38}$ is hydrogen, alkyl or phenyl; $R^{37}$ is alkyl; phenyl which can be substituted by alkyl, alkoxy, nitro or halogen; cycloalkyl or naphthyl, or $R^{37}$ together with $SO_2$—T forms a 5- or 6-membered ring together with $NR^3$ selected from the group consisting of the formulas:

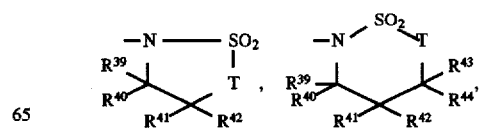

-continued

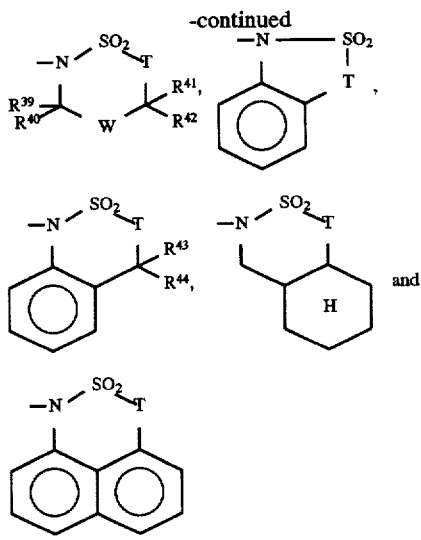

wherein $R^{39}$, $R^{40}$, $R^{41}$, $R^{42}$, $R^{43}$ and $R^{44}$ are independently hydrogen; alkyl; phenyl which can be substituted by alkyl, alkoxy, nitro or halogen; cycloalkyl or naphthyl, or $R^{39}$ and $R^{40}$, $R^{41}$ and $R^{42}$ or $R^{43}$ and $R^{44}$ can respectively form an oxo or alkylene; T is as defined above; W is O, S or $NR^{45}$ wherein $R^{45}$ is hydrogen, alkyl or phenyl, which comprises reacting an azetidinone derivative of the formula:

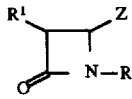

wherein R and $R^1$ are as defined above and Z is a leaving group, and an amide compound of the formula:

wherein $R^2$, $R^3$ and $R^4$ are as defined above, in the presence of a titanium compound of the formula:

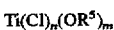

wherein $R^5$ is lower alkyl, n and m are independently an integer from 0 to 4; provided that n plus m always makes 4, and a base.

2. The process for the preparation according to claim 1, wherein $R^4$ is a substituent represented by the formula:

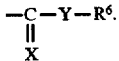

3. The process according to claim 1, wherein $R^4$ is a substituent of the formula:

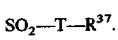

4. The process according to claim 1, wherein $R^4$ is a substituent of the formula:

5. The process according to claim 1, wherein $R^4$ is a substituent of the formula:

* * * * *